United States Patent
Cantiani et al.

(12)

(10) Patent No.: US 6,306,207 B2
(45) Date of Patent: Oct. 23, 2001

(54) SUPPLEMENTATION OF ESSENTIALLY AMORPHOUS CELLULOSE NANOFIBRILS WITH CARBOXYCELLULOSE WHICH HAS A HIGH DEGREE OF SUBSTITUTION

(75) Inventors: Robert Cantiani, Lyons; Gilles Guerin, Eaubonne; Alain Senechal, Charenton; Isabelle Vincent, Evreux; Joël Benchimol, Francqueville, all of (FR)

(73) Assignee: Rhodia Chimie, Boulogne Billancourt Cedex (FR)

( * ) Notice: Subject to any disclaimer, the term of this patent is extended or adjusted under 35 U.S.C. 154(b) by 0 days.

(21) Appl. No.: 09/782,802

(22) Filed: Feb. 14, 2001

Related U.S. Application Data

(62) Division of application No. 09/214,774, filed as application No. PCT/FR97/01291 on Jul. 11, 1997, now Pat. No. 6,224,663.

(30) Foreign Application Priority Data

Jul. 15, 1996 (FR) .................................................. 96 09062
Sep. 27, 1996 (FR) .................................................. 96 11779

(51) Int. Cl.$^7$ .............................. C08L 1/02; C08D 19/02
(52) U.S. Cl. ........................................ 106/162.8; 106/805
(58) Field of Search ................................. 106/162.8, 805

(56) References Cited

U.S. PATENT DOCUMENTS

| 4,481,076 | 11/1984 | Herrick | ................. | 162/158 |
| 4,659,388 | 4/1987 | Innami | ................. | 106/163.1 |
| 5,964,983 | 10/1999 | Diand | .................... | 162/27 |
| 6,224,663 | * 5/2001 | Cantiani et al. | .................. | 106/162.8 |

FOREIGN PATENT DOCUMENTS

| 0 102 829 | 3/1984 | (EP) | ................................ | D21C/5/00 |
| 0 198 094 | 10/1986 | (EP) | ................................ | A61K/7/16 |
| 0 537 554 | 4/1993 | (EP) . | | |
| WO 95/02966 | 2/1995 | (WO) | ................................ | A23L/1/05 |

* cited by examiner

*Primary Examiner*—David Brunsman
(74) *Attorney, Agent, or Firm*—Jean-Louis Seugnet

(57) ABSTRACT

The present invention relates to compositions comprising essentially amorphous cellulose nanofibrils, at least one additive chosen from carboxycellulose with a degree of substitution of more than 0.95, a natural polysaccharide, a polyol, and optionally at least one co-additive, the content of additive and of optional co-additive being less than or equal to 30% by weight relative to the weight of nanofibrils and of additive and of optional co-additive. Similarly, a subject of the invention is a process for preparing such compositions, which consists in adding the additive and the optional co-additive to a suspension of essentially amorphous nanofibrils, and then in drying the suspension thus supplemented. The compositions obtained are readily redispersable and conserve their initial rheological properties.

1 Claim, No Drawings

SUPPLEMENTATION OF ESSENTIALLY AMORPHOUS CELLULOSE NANOFIBRILS WITH CARBOXYCELLULOSE WHICH HAS A HIGH DEGREE OF SUBSTITUTION

This application is a divisional application under 35 U.S.C. Section 371 of Application Ser. No. 09/214,774, filed on Sep. 08, 1999 now U.S. Pat. No. 6,224,663, which is the National Stage of application No. PCT/FR97/01291, filed Jul. 11, 1997.

The present invention relates to compositions comprising essentially amorphous cellulose nanofibrils, at least one additive chosen from carboxycellulose with a degree of substitution of more than 0.95, a natural polysaccharide, a polyol and optionally at least one co-additive, as well as to a process for their preparation.

The invention relates to the suspensions obtained from such compositions.

Cellulose microfibrils and nanofibrils are well-known compounds which are used as additives for modifying the texture of media into which they are introduced. In the case of fluid media, they modify their viscosity or even their rheological profile.

However, there is a problem with cellulose microfibrils and nanofibrils, which is that they are obtained in the form of an aqueous suspension whose solids content is relatively low, from about 1 to about 5% by weight approximately. The development of these products in such a form is thus not economically viable, either in terms of storage or transportation for example. It has thus been considered, naturally, to present them in a dry form. Unfortunately, when the cellulose microfibril or nanofibril suspensions are dried, very strong hydrogen bonds are created between the fibrils which make it necessary to use very high-shear means to redisperse these fibrils, when it is possible to resuspend them.

Attempts have been made to propose solutions to the problem of drying cellulose microfibrils. Thus, additives have been introduced during the preparation of microfibril suspensions, and more particularly at the time of the homogenization.

For example, U.S. Pat. No. 4,481,076 proposes drying the cellulose microfibrils obtained from wood pulp in the presence of additive. The contents which are most favourable for good redispersion after drying, and thus for a good viscosity level of the suspension, are from about 50 to about 100% by weight relative to the dry microfibrils. As may be observed, the amounts of additives introduced are very large. Moreover, these methods are not entirely satisfactory, even though it is possible in principle, to redisperse these dried microfibrils, since the means used for the redispersion are still very high-shear.

International patent application WO 95/02966 describes the supplementation of microcrystalline cellulose with xanthan gum or carboxymethylcellulose, with contents of less than 33% by weight relative to the weight of microcrystalline cellulose.

However, extremely high-shear conditions are used to suspend the dried cellulose, since they are carried out under the standard conditions for stirring formulations intended for applications in the food sector. The dried microfibrils can thus not be considered as easily redispersible.

The teaching provided by the prior art regarding the redispersion of microcrystalline cellulose microfibrils, and in particular those obtained from wood pulp, cannot be transposed to cellulose nanofibrils, obtained from cells with primary walls.

Firstly, the cellulose microfibrils obtained from wood are derived from secondary walls. This means that they have a greater than 70% degree of crystallinity. During the step of homogenization of the microfibrils obtained from wood, rather than observing a disentangling of the fibres, as is the case during the step of homogenization of the cellulose nanofibrils obtained from primary walls, these fibrils are found to break. Consequently the cellulose microfibrils obtained from secondary walls do not have the characteristics of amorphous fibrils, but, rather, have the characteristics of microcrystalline microfibrils.

Moreover, the morphologies of the microfibrils and nanofibrils are different. In point of fact, the microcrystalline microfibrils, for example obtained from cellulose with secondary walls, such as wood pulp, are conventionally in the form of aggregates from a few tens of nanometres to a few micrometres, consisting of elementary fibrils, which cannot be disentangled during the homogenization step. As regards the cellulose nanofibrils obtained from cells with primary walls, they have a diameter of not more than a few nanometres and have the appearance of filaments.

It is relatively well established that the difficulty in redispersing cellulose microfibrils or nanofibrils is associated with the existence of numerous hydrogen bonds between the fibrils, which are created during drying. Now, the number of hydrogen bonds per weight unit of cellulose is directly associated with the morphology of the said microfibrils or nanofibrils, and, more specifically, is proportional to their specific surface; the greater the specific surface, the larger the number of hydrogen bonds per weight unit of cellulose. Given the particular morphology of the cellulose nanofibrils obtained from cells with primary walls, the specific surface of these nanofibrils is much higher than that of the microfibrils. A person skilled in the art would thus logically expect to encounter greater difficulties in redispersing cellulose nanofibrils.

Thus, given the state of the art presented above, it could be envisaged that larger amounts of additive than those used for the microfibrils would be necessary in order to obtain good redispersion of the dried nanofibrils.

However, the present invention has shown, against all expectations, that relatively low amounts of additive are sufficient to allow good redispersion of the dried nanofibrils, and without it being necessary to use extremely high-shear conditions. In addition, it has been found, surprisingly, that amounts of the order of those recommended in the prior art have considerable drawbacks as regards conserving the rheological properties of the nanofibrils.

This arises from the difference in behaviour between the crystalline microfibrils, for example the cellulose microfibrils obtained from secondary walls, and the nanofibrils obtained from cells with primary walls.

The reason for this is that the non-supplemented microcrystalline microfibrils are not dispersible in aqueous medium; they separate out by settling as soon as the stirring is stopped, even when very high-shear stirring means are used. Furthermore, they do not give shear-thinning rheological properties.

On the other hand, the nanofibrils obtained from primary walls are of a nature which is dispersible in aqueous medium. In addition, they give a quite specific rheological profile, of shear-thinning type, to the medium into which they are introduced.

Now, in general, drying adversely affects not only the capacity for redispersion of the dried nanofibrils and their viscosity, but also their rheological profile. Thus, large amounts of additives of the type usually used to redisperse microcrystalline microfibrils, such as those obtained from wood, i.e. as much additive as microfibrils, do not give good results as regards the shear-thinning rheological profile of the cellulose nanofibrils obtained from primary walls: the profile becomes more Newtonian, i.e. less shear-thinning.

As may be observed, the consequences of drying essentially amorphous cellulose nanofibrils in terms of the redispersion of these fibrils and their rheological properties (viscosity at low and high shear, rheological profile) cannot be solved in a satisfactory manner based on the knowledge obtained from the supplementation of microcrystalline microfibrils, for example of microfibrils obtained from cells with secondary walls.

The present invention thus provides a simple and effective solution to these problems.

These aims and others are achieved by the present invention, a first subject of which is a composition comprising essentially amorphous cellulose nanofibrils, at least one additive chosen from carboxycellulose with a degree of substitution of more than 0.95, a natural polysaccharide, a polyol and optionally at least one co-additive, the content of additive and of optional co-additive being less than or equal to 30% by weight relative to the weight of nanofibrils and of additive and optional co-additive.

Another subject of the present invention consists of a process for preparing a composition, in which cellulose nanofibrils are prepared from cellulosic pulp by carrying out at least one extraction, optionally followed by at least one step of bleaching the pulp thus treated, after which the resulting pulp is separated out and a homogenization step is carried out in at least one cycle, the characteristic of the process being that the following steps are carried out:

at least some of the additive and optionally co-additive(s) are added to the nanofibril suspension which has optionally undergone at least one homogenization cycle, a step of drying the suspension thus supplemented is carried out.

A third subject of the invention relates to a suspension comprising cellulose nanofibrils, which is obtained by redispersing the composition according to the invention.

The present invention makes it possible simultaneously to propose a process for drying essentially amorphous nanofibrils in the presence of additives, as well as compositions which are dried such that they are readily redispersible, while at the same time retaining the specific rheological properties of the initial, non-dried suspensions. Thus, the suspensions according to the invention, obtained after redispersing the compositions, have a good level of viscosity at a low shear gradient, as well as a rheological profile of shear-thinning type.

In addition, the means used to redisperse the dried compositions according to the invention are considerably less shearing than those usually used to redisperse dried microfibrils obtained from wood or from other secondary walls.

Other characteristics and advantages of the present invention will emerge more clearly on reading the description and the examples which follow.

As has been mentioned previously, the subject of the present invention is the supplementation of essentially amorphous cellulose nanofibrils.

The term "essentially amorphous" is intended to refer to nanofibrils whose degree of crystallinity is less than or equal to 50%. According to a specific variant of the present invention, the degree of crystallinity is between 15% and 50%. Preferably, the degree of crystallinity is less than 50%.

The cellulose nanofibrils treated according to the present invention are obtained from cells preferably consisting of at least about 80% primary walls. Preferably, the amount of primary walls is at least 85% by weight.

Such characteristics are present in particular in parenchymal cells. Sugar beet pulp, citrus fruits such as lemons, oranges and grapefruit, and most fruit and vegetables are examples of parenchyma.

Moreover, the nanofibrils forming part of the compositions according to the invention are, according to a particularly advantageous variant, charged at the surface with carboxylic acids and with acidic polysaccharides, alone or as a mixture.

The term "carboxylic acids" is intended to refer to simple carboxylic acids, as well as salts thereof. These acids are preferably chosen from uronic acids. More particularly, the said uronic acids are more particularly galacturonic acid and glucuronic acid.

As acidic polysaccharides, mention may be made of pectins, which are more particularly polygalacturonic acids. These acidic polysaccharides can be present as a mixture with hemicelluloses.

The cellulose nanofibrils also have a cross-section of between about 2 and about 10 nm. More particularly, the nanofibril cross-section is between about 2 and about 4 nm.

According to a particularly advantageous embodiment of the present invention, the nanofibrils forming part of the compositions according to the invention are obtained by using the treatment which will be described below. More particularly, this treatment is carried out on the pulp of vegetables with primary walls, such as, for example, beetroot pulp, after it has undergone a preliminary step of extraction of the sucrose, according to the methods known in the art.

Thus, the process comprises the following steps:
(a) first acidic or basic extraction, after which a first solid residue is recovered,
(b) optionally, second extraction, carried out under alkaline conditions, of the first solid residue, after which a second solid residue is recovered,
(c) washing of the first or second solid residue,
(d) optionally, bleaching of the washed residue,
(e) dilution of the third solid residue obtained after step (d) so as to obtain a solids content of between 2 and 10% by weight,
(f) homogenization of the dilute suspension.

In step (a), the term "pulp" is intended to refer to wet, dehydrated pulp stored by ensilage or partially depectinized.

The extraction step (a) can be carried out in acidic medium or in basic medium.

For an acidic extraction, the pulp is suspended in an aqueous solution for a few minutes so as to homogenize the acidified suspension at a pH of between 1 and 3, preferably between 1.5 and 2.5.

This operation is carried out with a concentrated solution of an acid such as hydrochloric acid or sulphuric acid.

This step may be advantageous for removing the calcium oxalate crystals which may be present in the pulp, and which, on account of their highly abrasive nature, can cause difficulties in the homogenization step.

For a basic extraction, the pulp is added to an alkaline solution of a base, for example sodium hydroxide or potassium hydroxide, with a concentration of less than 9% by weight, more particularly less than 6% by weight. Preferably, the concentration of the base is between 1 and 2% by weight.

A small amount of a water-soluble antioxidant, such as sodium sulphite $Na_2SO_3$, may be added in order to limit the oxidation reactions of the cellulose.

Step (a) is generally carried out at a temperature of between about 60° C. and 100° C., preferably between about 70° C. and about 95° C.

The duration of step (a) is between about 1 hour and about 4 hours.

During step (a), partial hydrolysis takes place with release and solubilization of most of the pectins and hemicelluloses, while at the same time retaining the molecular mass of the cellulose.

The solid residue is recovered from the suspension obtained from step (a) by carrying out known methods. Thus, it is possible to separate the solid residue by centrifugation, by filtration under vacuum or under pressure, with filter gauzes or filter presses, for example, or else by evaporation.

The first solid residue obtained is optionally subjected to a second extraction step carried out under alkaline conditions.

A second extraction step, step (b), is carried out when the first step has been carried out under acidic conditions. If the first extraction has been carried out under alkaline conditions, the second step is optional.

According to the process, this second extraction is carried out with a base preferably chosen from sodium hydroxide and potassium hydroxide, whose concentration is less than about 9% by weight, preferably between about 1% and about 6% by weight.

The duration of the alkaline extraction step is between about 1 and about 4 hours. It is preferably equal to about 2 hours.

After this second extraction, if it is carried out, a second solid residue is recovered.

In step (c), the residue derived from step (a) or (b) is washed thoroughly with water in order to recover the residue of cellulosic material.

The cellulosic material from step (c) is then optionally bleached, in step (d), according to the standard methods. For example, a treatment with sodium chlorite, with sodium hypochlorite or with hydrogen peroxide in a proportion of 5–20% relative to the amount of solids treated can be carried out.

Different concentrations of bleaching agent can be used, at temperatures of between about 18° C. and about 80° C., preferably between about 50° C. and about 70 °C.

The duration of this step (d) is between about 1 hour and about 4 hours, preferably between about 1 hour and about 2 hours.

A cellulosic material containing between 85 and 95% by weight of cellulose is thus obtained.

After this bleaching step, it may be preferable to wash the cellulose thoroughly with water.

The resulting suspension, which has optionally been bleached, is then rediluted in water in a proportion of 2 to 10% solids (step (e)), before undergoing a homogenization step (step (f)) comprising at least one cycle.

According to a first variant of the invention, the nanofibrils are supplemented before undergoing the homogenization step.

According to a second variant of the invention, the cellulose nanofibrils are supplemented after they have undergone at least one homogenization cycle.

The homogenization step corresponds to a mixing or blending operation or any operation of high mechanical shear, followed by one or more passages of the cell suspension through an orifice of small diameter, subjecting the suspension to a pressure drop of at least 20 MPa and to a high-speed shear action, followed by a high-speed deceleration impact.

The mixing or blending is carried out, for example, by passage(s) through the mixer or blender for a period ranging from a few minutes to about an hour, in a machine such as a Waring Blendor fitted with a four-blade impeller or a pan mill mixer or any other type of blender, such as a colloidal mill.

The actual homogenization will advantageously be carried out in a homogenizer such as a Manton Gaulin in which the suspension is subjected to a shear action at high speed and high pressure in a narrow passage and against an impact ring. Mention may also be made of the Micro Fluidizer, which is a homogenizer mainly consisting of a compressed-air motor which creates very high pressures, an interaction chamber in which the homogenization operation takes place (elongational shear, impacts and cavitations) and a low-pressure chamber which allows depressurization of the dispersion.

The suspension is introduced into the homogenizer preferably after preheating to a temperature of between 40 and 120° C., preferably between 85 and 95° C.

The temperature of the homogenization operation is maintained between 95 and 120° C., preferably above 100° C.

The suspension is subjected to pressures of between 20 and 100 MPa and preferably above 50 MPa in the homogenizer.

Homogenization of the cellulosic suspension is obtained by a number of passages which can range between 1 and 20, preferably between 2 and 5, until a stable suspension is obtained.

The homogenization operation can advantageously be followed by a high mechanical shear operation, for example in a machine such as the Sylverson Ultra Turrax.

It should be noted that this process has been described in European patent application EP 726,356 filed on 07/02/96, and reference may thus be made thereto if necessary. Example 20 of that text in particular gives a method for preparing a suspension of essentially amorphous cellulose nanofibrils.

The additives will now be described.

The first additive, or simply the additive, forming part of the composition according to the invention is chosen from carboxycellulose, in salt or acid form, with a degree of substitution of more than 0.95, a natural polysaccharide and a polyol.

The additives mentioned can be present alone or as mixtures.

According to a first embodiment, the additive of the composition according to the invention consists of carboxycellulose with a specific degree of substitution.

The cellulose used as additive is more particularly carboxymethylcellulose. Cellulose is a polymer consisting of glucose monomer units. The carboxyl group is introduced in a manner which is known per se, by reacting chloroacetic acid with cellulose.

The degree of substitution corresponds to the number of carboxymethyl groups per glucose unit. The maximum theoretical degree is 3.

According to the invention, the degree of substitution of carboxymethylcellulose is therefore more than 0.95.

The degree of polymerization of the carboxycellulose used as nanofibril additive, in accordance with the present invention, varies within a wide range. Thus, carboxymethylcelluloses of high masses (high degree of polymerization, high viscosity) or of low masses (low degree of polymerization, low viscosity) are suitable.

In the first category, mention may be made of celluloses whose viscosity is between about 9000 mPa.s, measured in an aqueous 1% solution (Brookfield, 30 rpm), and 250 mPa.s, measured in an aqueous 6% solution (Brookfield, 60 rpm).

In the second category, mention may be made of celluloses whose viscosity is between about 250 mPa.s, measured in an aqueous 6% solution (Brookfield, 60 rpm), and 10 mPa.s, measured in an aqueous 6% solution (Brookfield, 60 rpm).

In the case of the first category, the carboxycellulose content is less than or equal to 30% by weight.

In the case of the second category, the carboxycellulose content is more particularly between 10 and 30% by weight.

The additive forming part of the composition according to the invention can also be a natural polysaccharide.

Thus, the polysaccharide can be of bacterial, animal or plant origin.

Polysaccharides are polymers comprising saccharide units. Polysaccharides in an anionic or nonionic form are preferably used.

Among the suitable anionic polysaccharides, mention may be made, without intending to be limited thereto, of xanthan gum, succinoglycans, carrageenans and alginates.

As nonionic polysaccharides, mention may be made, for example, of galactomannans, such as guar gum and carob gum. Starch and its nonionic derivatives are also suitable, as well as nonionic cellulose derivatives.

According to a specific embodiment of the invention, an anionic polysaccharide, and more especially xanthan gum, is used as additive.

Among the suitable polyols, mention may be made most particularly of polyvinyl alcohol.

One preferred embodiment of the present invention consists of a composition whose additive is the carboxycellulose as defined.

A second specific embodiment consists of an additive comprising a polysaccharide, preferably an anionic polysaccharide, optionally combined with the abovementioned carboxycellulose.

The composition according to the invention can also comprise at least one co-additive chosen from:
  carboxycellulose with a degree of substitution of less than or equal to 0.95, preferably carboxymethylcellulose,
  saccharide monomers or oligomers,
  compounds of formula $(R^1R^2N)COA$, in which formula $R^1$ and $R^2$, which may be identical or different, represent hydrogen or a $C_1$–$C_{10}$, preferably $C_1$–$C_5$, alkyl radical, A represents hydrogen, a $C_1$–$C_{10}$, preferably $C_1$–$C_5$, alkyl radical or alternatively the group $R'^1 R'^2N$ with $R'^1$ and $R'^2$, which may be identical or different, representing hydrogen or a $C_1$–$C_{10}$, preferably $C_1$–$C_5$, alkyl radical,
  cationic or amphoteric surfactants, it being possible for these co-additives to be used alone or as a mixture.

It should be noted that the observations made above regarding the nature and viscosities of the carboxycellulose, and more particularly the carboxymethylcellulose with a high degree of substitution, remain valid here, with the exception of the degree of substitution.

Among the saccharide monomers or oligomers, mention may be made most particularly, and without intending to be limiting, of sorbitol, sucrose and fructose.

As regards the compounds of the type $(R^1R^2N)COA$, it is preferred to use compounds comprising two amide functions. Preferably, urea is used as co-additive.

Among the cationic surfactants, mention may be made of cationic quaternary ammonium derivatives such as, for example, cationic imidazoline derivatives, alkyltrimethylammonium, dialkyldimethylammonium, alkyldimethylbenzylammonium or alkyldimethylethylammonium halides and Quat esters.

As examples of suitable cationic compounds, mention may be made of the products sold by Rhône-Poulenc from the Rhodaquat range. It is also possible to use synthetic cationic polymers, known under the CTFA generic name of "Polyquaternium", for example the polymers Mirapol A15® or Mirapol 550® from the company Rhône-Poulenc.

The surfactants forming part of the formulation according to the invention can also be chosen from amphoteric surfactants. For example, mention may be made, without intending to be limiting, of alkylpolyamine amphoteric derivatives, alkylbetaines, alkyldimethylbetaines, alkylamidopropylbetaines, alkylamidopropyldimethylbetaines, alkyltrimethylsulphobetaines, imidazoline derivatives such as alkyl amphoacetates, alkyl amphodiacetates, alkyl amphopropionates, alkyl amphodipropionates, alkylsultaines or alkylamidopropylhydroxysultaines, and the condensation products of fatty acids and of protein hydrolysates, it being possible for these compounds to be used alone or as a mixture.

The surfactants Mirapon® Excel, Mirataine® CBS, Mirataine® CB, Mirataine H2CHA®, Ampholac 7T/X®, Ampholac 7C/X, the Miranol® range, Amphionic® SFB and Amphionic® XL may in particular be suitable for carrying out the present invention.

When the compositions according to the invention comprise one or more of the abovementioned co-additives, their content is less than 30% by weight relative to the weight of nanofibrils and of additive and of co-additive. Needless to say, the content of additive(s) and of co-additive(s) is such that it is less than or equal to 30% relative to the weight of nanofibrils, of additive(s) and of co-additive(s).

According to a first specific variant of the invention, the compositions comprise at least one additive, as well as at least one co-additive chosen from carboxycellulose with a degree of substitution of less than or equal to 0.95, saccharide monomers and oligomers or compounds of formula $(R^1R^2N)COA$.

In the case of this first variant, the co-additive content is less than 30% and preferably between 1 and 25% by weight relative to the weight of nanofibrils and of additive and of co-additive.

According to a second specific variant of the invention, the compositions comprise at least one additive and, as co-additive, at least one compound chosen from cationic and amphoteric surfactants.

In the case of this second variant, the co-additive content is between 1 and 10% by weight relative to the weight of nanofibrils and of additive and of co-additive.

In each of the two variants, the content of additive is less than or equal to 30% by weight relative to the weight of nanofibrils and of additive and of co-additive.

In the case of redispersion additives such as carboxycellulose with a high degree of substitution (degree of substitution of more than 0.95) or of co-additives such as cellulose with a low degree of substitution (degree of substitution of less than or equal to 0.95), the higher its concentration, the more it lowers the shear-thinning nature of the cellulose nanofibrils by modifying their state of dispersion in the water. Thus, in the case of carboxycellulose and for concentrations of greater than 30% by weight relative to the weight of nanofibrils and of additive and of co-additive, although the nanofibrils are redispersible, their rheological profile becomes more Newtonian, i.e. less shear-thinning, which is undesirable.

In the case of the use of carboxycellulose with a high degree of substitution, in comparison with a carboxycellulose with a low degree of substitution, it has been observed that the carboxycellulose with a high degree of substitution proves to be more effective in terms of its redispersing power and its maintenance of the shear-thinning rheological profile of the cellulose nanofibrils. Thus, for a similar mass of carboxycellulose, the required concentration of carboxycellulose with a high degree of substitution can advantageously be reduced relative to a carboxycellulose with a low degree of substitution.

Thus, the said content of additive and of optional Co-additive can be chosen to be less than or equal to 25% by weight relative to the weight of nanofibrils and additive and of optional co-additive; this content is preferably between 5% and 25% by weight relative to the same reference; thus, the cellulose nanofibrils redisperse easily and retain their shear-thinning rheological properties.

It should be noted that the use of such co-additives described above makes it possible, in combination with carboxymethylcellulose, to reinforce the shear-thinning profile of the cellulose nanofibrils after redispersion.

In addition, the compositions according to the invention have a solids content of at least 40% by weight. More particularly, the solids content is at least 60% by weight and is preferably at least 70% by weight.

Advantageously, it has been noted that the rheological profile of suspensions dried until a solids content of this order is obtained is not adversely affected.

The particle size of the composition according to the invention can vary within a wide range. It is usually between 1 $\mu$m and a few millimetres.

The process for preparing the compositions will now be described in greater detail.

The process according to the invention consists firstly in preparing the cellulose nanofibrils from appropriate cellulosic pulp, by carrying out a hydrolysis, optionally followed by at least one step of bleaching of the pulp thus treated. Everything which has been mentioned previously in this respect remains valid and will not be repeated here.

The process for preparing the compositions according to the invention consists, in a first step, in adding at least some of the additive and optionally co-additive(s) to the nanofibril suspension, which has optionally undergone at least one homogenization cycle. Next, in a second step, a step of drying the suspension thus supplemented is carried out.

According to a first advantageous variant of the present invention, the addition of at least some of the additive and optionally co-additive(s) is carried out after the homogenization step.

One particularly suitable embodiment of the invention consists in adding at least some of the additive and optionally co-additive(s) to the suspension after the homogenization step, after this suspension has undergone at least one concentration step.

The concentration step(s) take place by filtration, centrifugation or evaporation of some of the water from the suspension. It is possible, for example, to use filters under vacuum or under pressure, spraying towers, ovens or microwave ovens.

It is thus possible to carry out a precipitation, for example in an alcohol such as ethanol, isopropanol or any other similar alcohol to carry out a process of separation by freezing-thawing, by dialysis against a hygroscopic solution in which the size of the molecules is greater than the size of the pores in the membrane used.

These methods are cited merely as guides and cannot be considered as an exhaustive list.

According to this embodiment, the concentration operation can be carried out until a solids content of about 35% by weight is obtained. More particularly, the solids content is between 5 and 25% by weight.

The introduction of the additive and optionally co-additive(s) is carried out in a manner which is known per se, i.e. by any means which allows homogeneous introduction of a solution, a suspension or a powder to a suspension which tends to have the consistency of a paste. For example, mention may be made of blenders, extruders and mixers.

This operation can be carried out over a wide temperature range, more particularly between room temperature and 80° C. It may be advantageous to carry out the introduction at the temperature at which the concentration took place. It should also be noted that temperatures from about 50 to about 80° C. can also facilitate the addition of the additive, by decreasing its viscosity, for example.

A second embodiment of the process consists in adding at least some of the additive and optionally co-additive(s) to the suspension after the homogenization step, before this suspension has undergone at least one concentration step.

In this latter case, the concentration step(s) which take place after the addition of additive and optionally of co-additive are carried out in the same way as indicated above.

If this first variant is carried out, a preferred embodiment of the invention is to carry out the supplementation after the suspension has undergone one or more concentration steps.

According to a second advantageous variant of the present invention, the addition of at least some of the additive and optionally co-additive(s) is carried out before or during the homogenization step. When it is indicated that the supplementation takes place during the homogenization step, this means that the additive and optionally the co-additive(s) are introduced when the pulp has undergone at least one cycle of the homogenization step.

The supplementation takes place according to the methods indicated in the context of the first variant.

Prior to the actual drying step, it may be advantageous to carry out a shaping of the suspension which has been concentrated as mentioned previously.

This shaping is carried out in a manner which is known to those skilled in the art. Mention may be made in particular, without, however, intending to be limited thereto, of extrusion and granulation.

The first is carried out in standard apparatus comprising any type of die, and the second can be carried out, for example, in drums or granulators.

The drying is carried out by any means which is known to those skilled in the art, provided that this means makes it possible to have good homogeneity of the temperature of the shaped or unshaped suspension.

In this respect, mention may be made of evaporation in ovens on a conveyor belt, with or without induction, radiative or non-radiative, rotating ovens or fluidized beds, or in a freeze-dryer.

According to a particularly advantageous variant of the present invention, the drying step is carried out so as to maintain not less than 3% by weight of water relative to the weight of the solid obtained. More particularly, the weight of water maintained is between 10 and 30% by weight. Such an implementation makes it possible not to exceed the threshold beyond which redispersion of the nanofibrils may no longer be complete.

The drying advantageously takes place in air, although it may be envisaged to carry it out under an inert gas, such as nitrogen.

It should also be noted that it is preferred to carry out the drying in an atmosphere whose degree of humidity is controlled so as to be able to maintain the desired moisture content in the composition.

The drying temperature should limit any degradation of the carboxylic acids, of the acidic polysaccharides, of the hemicelluloses and/or of the additives and co-additives. It is more particularly between 30 and 80° C., preferably between 30 and 60° C.

It should be noted that it would not constitute a departure from the context of the present invention to carry out a drying operation in several steps, some of which would use the means indicated above for the concentration step.

After the drying step, the composition obtained can be blended.

If such a possibility is selected, the particle size of the powder is generally between 1 µm and a few millimetres. preferably between 30 µm and a few millimetres. Such a particle size makes it possible to facilitate redispersion to a certain extent while at the same time limiting handling problems.

Another subject of the present invention consists of a suspension of cellulose nanofibrils which is obtained by redispersion of the supplemented composition according to the invention in water or any other medium.

Besides the fact that it can be obtained by redispersion of the composition according to the invention, the suspension according to the invention has a rheological profile of shear-thinning type.

Moreover, it has a level of viscosity corresponding to at least 50%, for a shear rate of at least $1s^{-1}$, of the level of viscosity of a cellulose nanofibril suspension which has not undergone a drying step and which does not comprise additives or co-additives.

A subject of the present invention is also the use of carboxycellulose, preferably carboxymethylcellulose, and optionally of co-additives, with essentially amorphous cellulose nanofibrils, with the aim of conserving a shear-thinning rheological profile for a suspension comprising essentially amorphous cellulose nanofibrils which have undergone a drying step.

Everything which has been mentioned previously regarding the additives, co-additives and the other elements which make up the composition according to the invention, as well as the preparation of the said composition, remains valid and reference may be made thereto.

The compositions according to the invention and the suspensions obtained by redispersion of these compositions can be used in many sectors in which it is desired to have a shear-thinning rheological profile. This may be the case for fluids used in petroleum exploitation, for formulations intended for the cosmetics, detergency or food sectors, or alternatively public works and construction.

Concrete but in no way limiting examples will now be given.

COMPARATIVE EXAMPLE 1

The Comparative Example is carried out in the absence of additive and co-additive.

The stock nanofibril dispersion used contains 2.3% by weight of cellulose nanofibrils, supplied by Générale Sucrière, and is prehomogenized with an Ultra-Turrax machine at 14,000 rpm (1 min per 100 g of dispersion).

This non-dried stock dispersion is then diluted to 0.3% by weight of cellulose nanofibrils in distilled water using the Ultra-Turrax machine at 8000 rpm for 1 min. This constitutes the control solution.

The same stock dispersion is concentrated to a solids content of 40% using a filter press. The solid obtained is then redispersed to 0.3% by weight of cellulose nanofibrils in distilled water. The stirring is carried out using the Ultra-Turrax machine at 8000 rpm for 1 min. Mixture 1 is thus obtained.

Flow rheology is carried out after 24 hours on a RFS 8400 rheometer in Couette geometry (scanning in shear gradient between 1 and 100 $s^{-1}$).

The results are summarized in Table 1.

TABLE 1

| Shear gradient ($s^{-1}$) | Viscosity (Pa.s) Control | Viscosity (Pa.s) Mixture 1 |
| --- | --- | --- |
| 1.27 | 3.0 | $2.0 \times 10^{-1}$ |
| 2.01 | 1.3 | $9.6 \times 10^{-2}$ |
| 5.05 | $4.3 \times 10^{-1}$ | $4.2 \times 10^{-2}$ |
| 12.7 | $1.6 \times 10^{-1}$ | $2.3 \times 10^{-2}$ |
| 20.1 | $9.9 \times 10^{-2}$ | $1.8 \times 10^{-2}$ |
| 50.5 | $3.2 \times 10^{-2}$ | $8.8 \times 10^{-3}$ |
| 80.0 | $1.6 \times 10^{-2}$ | $6.4 \times 10^{-3}$ |

In mixture 1, it is observed that the decantation volume (the supernatant) reaches 10% after standing for 4 hours and exceeds 15% after standing for 24 hours, whereas the control remains stable.

Furthermore, the recovered viscosity, after concentration without an additive and redispersion, is only 7% of the initial viscosity for a shear gradient of greater than or equal to 1 $s^{-1}$.

The Comparative Example shows that in the absence of additive such as carboxymethylcellulose with a high degree of substitution, drying of the cellulose nanofibrils followed by redispersion with a high-shear machine (Ultra-Turrax) leads to an unstable dispersion which loses 93% of its initial viscosity for a shear gradient of greater than or equal to 1 $s^{-1}$.

COMPARATIVE EXAMPLE 2

The aim of this example is to show the different behaviour of microcrystalline cellulose microfibrils.
1) Preparation of the Systems Based on Cellulose Microfibrils and on Carboxymethylcellulose with a High Degree of Substitution The carboxymethylcellulose Blanose 12M8P® is dissolved in distilled water.

The solution is then added to a suspension of Acticel 12® (Active Organics) cellulose microfibrils and the mixture is stirred with an Ultra-Turrax machine at 14,000 rpm for 5 min.

The amount of carboxymethylcellulose added is 15% by weight relative to the weight of cellulose microfibrils and carboxymethylcellulose.

The mixture is then poured into crucibles, after which it is dried in an oven to a solids content of 97%, controlled by assaying the water by the Karl-Fischer method.

The dried mixture is then blended in a coffee mill, and then screened through a 500 µm screen.
2) Redispersion of the Systems based on Cellulose Microfibrils and on Carboxymethylcellulose with a High Degree of Substitution, and Characterization The powder obtained is redispersed at 0.3% by weight of cellulose microfibrils in distilled water. (a) Stirring is carried out using a deflocculating paddle at 1000 rpm for 30 min.

Five minutes after stopping the stirring, a separation by settling takes place in which the supernatant represents 91% of the volume. (b) The stirring is carried out with an Ultra-Turrax machine at 14,000 rpm for 5 min.

Five minutes after stopping the stirring, a separation by settling takes place in which the supernatant represents 91% of the volume.

This example shows that there is no redispersion of the microfibrils, even when they are subjected to very high shear conditions. Consequently, contents of as low as 15% additive relative to the microcrystalline microfibrils cannot be used to redisperse the microfibrils after drying.

COMPARATIVE EXAMPLE 3

The aim of this example is to show the different behaviour of microcrystalline cellulose microfibrils.

1) Preparation of the Systems Based on Cellulose Microfibrils and on Xanthan Gum:

Comparative Example 2 is reproduced, except that the additive is xanthan gum (Rhodopol 23®) and the amount is 30% by weight relative to the weight of cellulose microfibrils and xanthan gum.

2) Redispersion of the Systems Based on Cellulose Microfibrils and on Xanthan Gum, and Characterization The powder obtained is redispersed at 0.3% by weight of cellulose microfibrils in distilled water. (a) Stirring is carried out with a deflocculating paddle at 1000 rpm for 30 min.

5 minutes after stopping the stirring, a separation by settling takes place in which the supernatant represents 90% of the volume. (b) The stirring is carried out with an Ultra-Turrax machine at 14,000 rpm for 5 min.

5 minutes after stopping the stirring, a separation by settling takes place in which the supernatant represents 90% of the volume.

This example shows that there is no redispersion of the microfibrils, even when they are subjected to very high shear conditions. Consequently, contents of about 30% additive relative to the microcrystalline microfibrils cannot be used to redisperse the microfibrils after drying.

EXAMPLE 4

1) Preparation of the Systems Based on Cellulose Nanofibrils and on Carboxymethylcellulose with a High Degree of Substitution The carboxymethylcellulose (degree of substitution equal to 1.2; of moderate viscosity—product Drilling Specialities Company—Drispac Superlo) is dissolved in distilled water.

The solution is then added to the nanofibril stock dispersion (2.9% of cellulose nanofibrils supplied by Generale Sucriere and prehomogenized with an Ultra-Turrax machine at 14,000 rpm (1 min per 100 g of dispersion)) and the mixture is stirred with a deflocculating paddle at 1000 rpm for 30 min.

The amount of carboxymethylcellulose added is from 15 to 30% by weight relative to the weight of cellulose nanofibrils and of carboxymethylcellulose.

The mixture is then poured into crucibles, after which it is dried in a ventilated oven at 40° C., to a solids content of 93%, which is controlled by assaying the water by the Karl-Fischer method.

The dried mixture is then blended in a coffee mill, after which it is screened through a 500 μm screen.

2) Redispersion of the Systems Based on Cellulose Nanofibrils and on Carboxymethylcellulose with a High Degree of Substitution, and Characterization The powder obtained is redispersed at 0.3% by weight of cellulose nanofibrils in distilled water. Stirring is carried out using a deflocculating paddle at 1000 rpm for 5 min or 30 min.

Flow rheology is carried out after 24 hours on an RFS 8400 rheometer in Couette geometry (scanning in shear gradient between 1 and 100 $s^{-1}$).

All the systems are compared with the non-dried cellulose nanofibrils diluted in water to 0.3% with an Ultra-Turrax machine at 14,000 rpm for 1 min (optimum state of redispersion of the nanofibrils).

Table II shows the effect of the carboxymethylcellulose (Drispac Superlo) concentration on the rheological profile of the cellulose nanofibrils after redispersion.

TABLE II

| Shear gradient ($s^{-1}$) | Viscosity (Pa.s) | | |
| --- | --- | --- | --- |
| | Control | Mixture 1 | Mixture 2 |
| 1.27 | $4.1 \times 10^{-1}$ | $5.6 \times 10^{-1}$ | $2.9 \times 10^{-1}$ |
| 2.01 | $2.6 \times 10^{-1}$ | $4.2 \times 10^{-1}$ | $1.9 \times 10^{-1}$ |
| 5.05 | $1.3 \times 10^{-1}$ | $2.5 \times 10^{-1}$ | $1.1 \times 10^{-1}$ |
| 12.7 | $1.0 \times 10^{-1}$ | $1.5 \times 10^{-1}$ | $7.3 \times 10^{-2}$ |
| 20.1 | $6.0 \times 10^{-2}$ | $1.2 \times 10^{-1}$ | $5.4 \times 10^{-2}$ |
| 50.5 | $2.8 \times 10^{-2}$ | $7.2 \times 10^{-2}$ | $3.5 \times 10^{-2}$ |
| 80.0 | $2.5 \times 10^{-2}$ | $5.7 \times 10^{-2}$ | $2.7 \times 10^{-2}$ |

Control: non-supplemented, non-dried cellulose nanofibrils obtained from the stock dispersion, and diluted with an Ultra-Turrax machine for one minute at 14,000 rpm;

Mixture 1: 70% of nanofibrils and 30% of carboxymethylcellulose; redispersion with a deflocculating paddle at 1000 rpm for 5 min.

Mixture 2: 85% of nanofibrils and 15% of carboxymethylcellulose; redispersion with a deflocculating paddle at 1000 rpm for 30 min.

It should be noted that the suspensions obtained according to the invention are stable over time.

It is moreover observed that the addition of carboxymethylcellulose with a high degree of substitution allows the redispersion of dried nanofibrils and creates a state of dispersion of the nanofibrils such that, with 15% of additive, at least 72% of the viscosity of the non-dried nanofibril suspension is recovered, at a shear gradient of 1 $s^{-1}$, and with 30% of additive, at least 134% of the viscosity of the non-dried suspension is recovered.

In addition, the rheological profile of shear-thinning type is conserved.

EXAMPLE 5

1) Preparation of the Systems Based on Cellulose Nanofibrils, on Carboxymethylcellulose and on Sucrose The carboxymethylcellulose (degree of substitution equal to 1.2; of moderate viscosity—product Blanose 12M8P from Aqualon) is dissolved in distilled water.

The sucrose is also dissolved in distilled water.

The carboxymethylcellulose solution is then added to the nanofibril stock dispersion (3.1% of cellulose nanofibrils supplied by Générale Sucriére and prehomogenized with an Ultra-Turrax machine at 14,000 rpm—1 min per 100 g of dispersion) and this mixture is stirred using a deflocculating paddle at 1000 rpm for 30 min.

In the case of the mixture without co-additive (mixture 1), the amount of carboxymethylcellulose added is 15% by weight relative to the weight of cellulose nanofibrils and carboxymethylcellulose. In the presence of the co-additive (mixture 2), the amount of carboxymethylcellulose added is 10% by weight relative to the weight of cellulose nanofibrils and of carboxymethylcellulose and of co-additive.

The mixture is then poured into crucibles, after which it is dried in a ventilated oven at 40° C., to a solids content of 96%, which is controlled by assaying the water by the Karl-Fischer method.

The dried mixture is then blended in a coffee mill, after which it is screened through a 500 µm screen.

When the composition also comprises a co-additive, this is added to the stock dispersion at the same time as the additive.

The sucrose solution is then added to the nanofibril stock dispersion which has already been supplemented with carboxymethylcellulose, and this mixture is stirred using a deflocculating paddle at 1000 rpm for 30 min.

The amount of carboxymethylcellulose added is 10% and that of sucrose is 20% by weight, relative to the weight of cellulose nanofibrils and of carboxymethylcellulose and of sucrose (mixture 2).

The mixture is then poured into crucibles, after which it is dried in a ventilated oven at 40° C. to a solids content of 96%, which is controlled by assaying the water by the Karl-Fischer method.

2) Redispersion of the Systems Based on Cellulose Nanofibrils, on Carboxymethylcellulose and on Sucrose, and Characterization The powders obtained are redispersed at 0.3% by weight of cellulose nanofibrils in distilled water. Stirring is carried out using a deflocculating paddle at 1000 rpm for 30 min.

Flow rheology is carried out after 24 hours on an RFS 8400 rheometer in Couette geometry (scanning in shear gradient between 1 and 100 $s^{-1}$).

All the systems are compared with the control sample corresponding to the non-dried cellulose nanofibrils with a solids content of 3.1%, diluted in water to 0.3% using a deflocculating paddle at 1000 rpm for 5 min.

Mixture 1: 85% of nanofibrils and 15% of carboxymethylcellulose; redispersion using a deflocculating paddle at 1000 rpm for 30 min.

Mixture 2: 70% of nanofibrils. 10% of carboxymethylcellulose and 20% of sucrose (co-additive); redispersion using a deflocculating paddle at 1000 rpm for 30 min.

Table III shows the effect of the concentration of carboxymethylcellulose, as well as that of the co-additive, on the rheological profile of the cellulose nanofibrils after redispersion.

TABLE III

| Shear gradient | Viscosity (Pa.s) | | |
| --- | --- | --- | --- |
| ($s^{-1}$) | Control | Mixture 1 | Mixture 2 |
| $1.27 \times 10^{-1}$ | 2.0 | $4.3 \times 10^{-1}$ | 2.7 |
| $2.01 \times 10^{-1}$ | 1.2 | $3.4 \times 10^{-1}$ | 1.5 |
| $5.05 \times 10^{-1}$ | $2.8 \times 10^{-1}$ | $2.4 \times 10^{-1}$ | $5.3 \times 10^{-1}$ |
| 1.27 | $9.7 \times 10^{-2}$ | $1.1 \times 10^{-1}$ | $2.5 \times 10^{-1}$ |
| 2.01 | $6.2 \times 10^{-2}$ | $7.4 \times 10^{-2}$ | $1.8 \times 10^{-1}$ |
| 5.05 | $3.5 \times 10^{-2}$ | $4.0 \times 10^{-2}$ | $7.8 \times 10^{-2}$ |
| 12.7 | $2.7 \times 10^{-2}$ | $2.6 \times 10^{-2}$ | $4.6 \times 10^{-2}$ |
| 20.1 | $1.9 \times 10^{-2}$ | $2.1 \times 10^{-2}$ | $3.8 \times 10^{-2}$ |
| 50.5 | $1.6 \times 10^{-2}$ | $1.4 \times 10^{-2}$ | $2.6 \times 10^{-2}$ |
| 80.0 | $1.3 \times 10^{-2}$ | $1.1 \times 10^{-2}$ | $2.1 \times 10^{-2}$ |

It should be noted that the suspensions obtained according to the invention are stable over time.

It is observed that the addition of carboxymethylcellulose alone, with a high degree of substitution allows the redispersion of dried nanofibrils and makes it possible to create a state of dispersion of the nanofibrils such that, with 15% additive, at least 114% of the viscosity of the non-dried nanofibril suspension is recovered, for a shear gradient of greater than 1 $s^{-1}$, and at least 22% of the viscosity of the non-dried suspension is recovered, for a shear gradient in the region of 0.1 $s^{-1}$.

In the presence of co-additive, this recovery is 260% of the initial viscosity for a shear rate of greater than 1 $s^{-1}$, and 135% for a shear rate in the region of 0.1 $s^{-1}$. From these results, the partial replacement of the carboxymethylcellulose with sucrose makes it possible to increase the shear-thinning property of the nanofibrils.

EXAMPLE 6

1) Preparation of the Systems based on Cellulose Nanofibrils and on Xanthan Gum

The xanthan gum (Rhodopol 23®) is dissolved in distilled water.

The solution is then added to the nanofibril stock solution (2.9% of cellulose nanofibrils supplied by Generale Sucriere and prehomogenized using an Ultra-Turrax machine at 14,000 rpm (1 min per 100 g of dispersion)) and this mixture is stirred with a deflocculating paddle at 1000 rpm for 30 min.

The amount of xanthan gum added is 30% by weight, relative to the weight of cellulose nanofibrils and xanthan gum.

The mixture is subsequently poured into crucibles and then dried in a ventilated oven at 40° C., to a solids content of 97%, controlled by assaying the water by the Karl-Fischer method.

The dried mixture is then blended in a coffee mill, after which it is screened through a 500 µm screen.

2) Redispersion of the Systems Based on Cellulose Nanofibrils Arid on Xanthan Gum, and Characterization The powder obtained is redispersed at 0.3% by weight of cellulose nanofibrils in distilled water. Stirring is carried out using a deflocculating paddle at 1000 rpm for 30 min.

Flow rheology is carried out after 24 hours on an RFS 8400 rheometer in Couette geometry (scanning in shear gradient between 1 and 100 $s^{-1}$).

All the systems are compared with the non-dried cellulose nanofibrils diluted in water to 0.3% using an Ultra-Turrax machine at 14,000 rpm for 1 min (optimum state of redispersion of the nanofibrils).

Table IV shows the effect of xanthan gum on the rheological profile of the cellulose nanofibrils after redispersion.

TABLE IV

| Shear gradient | Viscosity (Pa.s) | |
| --- | --- | --- |
| ($s^{-1}$) | Control | Mixture 1 |
| 1.27 | $4.1 \times 10^{-1}$ | $10.0 \times 10^{-1}$ |
| 2.01 | $2.6 \times 10^{-1}$ | $6.0 \times 10^{-1}$ |
| 5.05 | $1.3 \times 10^{-1}$ | $3.0 \times 10^{-1}$ |
| 12.7 | $1.0 \times 10^{-1}$ | $1.5 \times 10^{-1}$ |
| 20.1 | $6.0 \times 10^{-2}$ | $1.0 \times 10^{-1}$ |
| 50.5 | $2.8 \times 10^{-2}$ | $5.0 \times 10^{-2}$ |
| 80.0 | $2.5 \times 10^{-2}$ | $3.8 \times 10^{-2}$ |

Control: Non-supplemented, non-dried cellulose nanofibrils, obtained from the stock dispersion and diluted using an Ultra-Turrax machine for 1 minute at 14,000 rpm, Mixture 1: 70% of nanofibrils and 30% of xanthan gum; redispersion using a deflocculating panel at 1000 rpm for 30 min.

It should be noted that the suspension obtained according to the invention is stable over time.

It is moreover observed that the addition of xanthan gum allows the redispersion of dried nanofibrils and makes it possible to create a state of dispersion of the nanofibrils such that, with 30% additive, at least 240% of the viscosity of the non-dried nanofibril suspension is recovered, at a shear gradient of 1 s$^{-1}$.

In addition, the theological profile of shear-thinning type is retained.

What is claimed is:

1. A process for conserving a shear-thinning rheological profile in a suspension comprising essentially amorphous cellulose nanofibrils which have undergone a drying step, said process comprising the step of adding to said suspension carboxycellulose, and optionally of co-additive, with amorphous cellulose nanofibrils.

* * * * *